United States Patent
Preciado

(10) Patent No.: US 11,751,765 B2
(45) Date of Patent: Sep. 12, 2023

(54) OPHTHALMIC IMAGING DEVICE

(71) Applicant: Optos Plc, Dunfermline (GB)

(72) Inventor: Miguel Angel Preciado, Dunfermline (GB)

(73) Assignee: Optos Plc, Dunfermline (GB)

( * ) Notice: Subject to any disclaimer, the term of this patent is extended or adjusted under 35 U.S.C. 154(b) by 297 days.

(21) Appl. No.: 17/036,201

(22) Filed: Sep. 29, 2020

(65) Prior Publication Data

US 2021/0093195 A1    Apr. 1, 2021

(30) Foreign Application Priority Data

Oct. 1, 2019  (EP) ..................................... 19200774
Oct. 4, 2019  (EP) ..................................... 19201433

(51) Int. Cl.
*A61B 3/15* (2006.01)
*G02B 26/02* (2006.01)
(Continued)

(52) U.S. Cl.
CPC .............. *A61B 3/156* (2013.01); *G02B 26/02* (2013.01); *G02B 26/0816* (2013.01);
(Continued)

(58) Field of Classification Search
CPC ....... G02F 1/137; G02B 26/101; G02B 26/02; A61B 2090/306; A61B 3/1561;
(Continued)

(56) References Cited

U.S. PATENT DOCUMENTS

| 5,815,242 A | 9/1998 | Anderson et al. |
| 7,959,290 B2 | 6/2011 | Cairns et al. |
| (Continued) | | |

FOREIGN PATENT DOCUMENTS

| EP | 2992814 A1 | 3/2016 |
| EP | 3235421 A1 | 10/2017 |
| (Continued) | | |

OTHER PUBLICATIONS

Notice of Reasons for Refusal (dated Nov. 2, 2021 and) issued in Japanese Patent Application 2020-167245 (2 sheets); English translation attached (3 sheets).
(Continued)

*Primary Examiner* — Christopher Stanford
*Assistant Examiner* — Journey F Sumlar
(74) *Attorney, Agent, or Firm* — Faegre Drinker Biddle & Reath

(57) ABSTRACT

An ophthalmic device for imaging an eye, wherein a scanning element scans a first portion of light beam across a region of an eye via a light guiding component and a second portion of the light beam is reflected back by the light guiding component. The ophthalmic device further comprises: a light detector to detect light reflected from eye and guided to the light detector by the light guiding component; and a dynamic amplitude mask which receives the light reflected from the eye and the light reflected back by the light guiding component, and has an unmasked portion to allow light reflected from the eye to reach the light detector, and a masked portion whose spatial distribution varies with a scan angle such that the masked portion prevents light reflected back by the light guiding component from reaching the light detector during the scan.

14 Claims, 11 Drawing Sheets

(51) Int. Cl.
  *G02B 26/08* (2006.01)
  *G02B 26/10* (2006.01)
  *G02F 1/137* (2006.01)
  *A61B 90/30* (2016.01)

(52) U.S. Cl.
  CPC ........... *G02B 26/101* (2013.01); *G02F 1/137* (2013.01); *A61B 2090/306* (2016.02)

(58) Field of Classification Search
  CPC ............ A61B 3/101; A61B 2018/2065; A61B 2018/1807; A61B 2017/00508; A61B 3/0025; A61B 18/20; A61B 5/0066; A61B 3/102

See application file for complete search history.

(56) References Cited

U.S. PATENT DOCUMENTS

| | | | |
|---|---|---|---|
| 10,610,096 B2* | 4/2020 | Scheibler | A61B 3/102 |
| 2018/0014727 A1 | 1/2018 | Bublitz et al. | |
| 2018/0104098 A1* | 4/2018 | Kurtz | A61F 9/008 |

FOREIGN PATENT DOCUMENTS

| | | |
|---|---|---|
| JP | H4-71526 | 3/1992 |
| JP | 2017148097 | 8/2017 |
| JP | 2018504219 | 2/2018 |
| JP | 2019134905 A | 8/2019 |

OTHER PUBLICATIONS

European Search Report dated May 4, 2020 in European patent application No. 19201433.0-1122.

* cited by examiner $(\theta = 10°, \varphi = 10°)$

|  | $y = 1$ | $y = 2$ | $y = 3$ | $y = 4$ |
|---|---|---|---|---|
| $x = 1$ | 0 | 0 | 1 | 1 |
| $x = 2$ | 0 | 0 | 1 | 1 |
| $x = 3$ | 1 | 1 | 1 | 1 |
| $x = 4$ | 1 | 1 | 1 | 1 |

Fig. 8A $(\theta = 10°, \varphi = 20°)$

|  | $y = 1$ | $y = 2$ | $y = 3$ | $y = 4$ |
|---|---|---|---|---|
| $x = 1$ | 1 | 1 | 1 | 1 |
| $x = 2$ | 1 | 1 | 1 | 1 |
| $x = 3$ | 1 | 1 | 0 | 0 |
| $x = 4$ | 1 | 1 | 0 | 0 |

Fig. 8B

OPHTHALMIC IMAGING DEVICE

CROSS REFERENCE TO RELATED APPLICATIONS

This application claims the benefit of priority based on European Patent Applications EP 19 200 774.8 filed Oct. 1, 2019 and EP 19 201 433.0 filed Oct. 4, 2019, the entireties of which are incorporated by reference as if set forth fully herein.

FIELD

Example aspects herein generally relate to the field of ophthalmic imaging devices and, more particularly, to ophthalmic scanners which acquire ocular images by scanning a light beam across the retina or other part of the eye via a light guiding component of the scanner and detecting light reflected from the eye which has been collected by the light guiding component.

BACKGROUND

In ophthalmic scanning imaging systems which perform ocular imaging using a light guiding component such as a lens barrel having an array of lenses, for example, reflection of some of the light (referred to herein as "back-reflection" and "back-reflected light") in a scanned light beam by the light guiding component may interfere with the measurement of light from the remainder of the light in the light beam which has propagated through the light guiding component, been reflected from the eye and guided to a light detector by the light guiding component, and thus introduce reflection-related artefacts into the generated ocular image. In a scanning laser ophthalmoscope (SLO), the effects of such internal reflections are suppressed to some degree by confocal detection.

SUMMARY

There is provided, in accordance with a first example aspect herein, an ophthalmic imaging device for imaging an eye, comprising a light guiding component and a scanning element, which is operable to scan a light beam across the light guiding component such that a first portion of the light beam incident on the light guiding component is guided by the light guiding component to scan across a region of the eye, and a second portion of the light beam incident on the light guiding component is reflected back by the light guiding component. The ophthalmic imaging device further comprises a light detector configured to detect light from the first portion of the light beam which has been reflected by the region of the eye and guided to the light detector by the light guiding component. The ophthalmic imaging device further comprises a dynamic amplitude mask, which is arranged in the ophthalmic imaging device so as to receive, from the light guiding component, the light from the first portion of the light beam which has been reflected by the region of the eye, and the light from the second portion of the light beam which has been reflected back by the light guiding component and is incident on the dynamic amplitude mask with a spatial intensity distribution that varies as a function of a scan angle of the light beam scanned by the scanning element. The dynamic amplitude mask has an unmasked portion configured to allow the received light from the first portion of the light beam, which has been reflected by the region of the eye, to propagate to the light detector, and a masked portion having a spatial distribution which is configured to vary as a function of the scan angle such that the masked portion prevents at least some of the light from the second portion of the light beam reflected back by the light guiding component from reaching the light detector as the first portion of the light beam is scanned across the region of the eye.

There is provided, in accordance with a second example aspect herein, an ophthalmic imaging device for imaging an eye, comprising a light guiding component and a scanning element operable to scan a light beam across the light guiding component such that a first portion of the light beam incident on the light guiding component is guided by the light guiding component to scan across a region of the eye, and a second portion of the light beam incident on the light guiding component is reflected back by the light guiding component. The ophthalmic imaging device further comprises a photodetector which is arranged in the ophthalmic imaging device so as to detect a spatial light intensity distribution, across a light-detection surface of the photodetector, of light incident on the light-detection surface which comprises the light from the first portion of the light beam which has been reflected by the region of the eye and guided to the photodetector by the light guiding component, and the light from the second portion of the light beam which has been reflected back by the light guiding component and is incident on the photodetector with a spatial intensity distribution over the light-detection surface of the photodetector that varies as a function of a scan angle of the light beam scanned by the scanning element. The ophthalmic imaging device further comprises an image processor configured to process the spatial light intensity distribution detected by the photodetector by applying a digital mask to the spatial light intensity distribution so as to reduce values of the detected light intensity in a masked portion of the detected spatial light intensity distribution that has been masked by the digital mask, and to generate image data based on the processed light intensity distribution. The masked portion has a spatial distribution which is configured to vary as a function of the scan angle so as to reduce a contribution of the light from the second portion of the light beam reflected back by the light guiding component to the generated image data as the first portion of the light beam is scanned across the region of the eye.

BRIEF DESCRIPTION OF THE DRAWINGS

Embodiments of the invention will now be explained in detail, by way of non-limiting example only, with reference to the accompanying figures described below. Like reference numerals appearing in different ones of the figures can denote identical or functionally similar elements, unless indicated otherwise.

FIG. 8A illustrates a first look-up table storing, for a first set of scanning beam angles, respective configuration information on the configuration of micromirror orientations in a digital micromirror array of the dynamic amplitude mask.

FIG. 8B illustrates a second look-up table storing, for a second set of scanning beam angles, respective configuration information on the configuration of micromirror orientations in a digital micromirror array of the dynamic amplitude mask.

DETAILED DESCRIPTION OF EXAMPLE EMBODIMENTS

Although adverse effects of unwanted back-reflection from optical element(s) in the light guiding component of an SLO on an acquired ocular image may be suppressed by reducing the size of the aperture used in confocal detection, doing so tends to reduce the signal-to-noise ratio (SNR) in the acquired ocular image. Furthermore, the present inventor has recognised that the spatial intensity distribution of the back-reflections may change dynamically with the scan angle of the scanning beam as the scan beam is scanned across the retina or other part of the eye, with strong reflections being observed at certain scan angles in many imaging systems. The present inventor has found that the reflection-based image artefacts in acquired ocular images can be effectively suppressed, whilst achieving an improved SNR, by adapting the ophthalmic imaging device to include a dynamic amplitude mask, which is configured to vary its mask configuration with the scan angle of the imaging light beam. The dynamic amplitude mask may be a physical device or it may be implemented digitally, as explained in more detail below. The spatial intensity distribution of the back-reflected light in any suitable plane in the ophthalmic imaging device, such as an imaging plane or a Fourier plane of the ophthalmic imaging device, for example, may be determined for different scan angles in a calibration process, and used to configure the dynamic amplitude mask so that it can prevent at least some of the back-reflected light from contributing to the image formed by the light detector of the ophthalmic imaging device as the scan angle is varied during the course of a subsequently performed scan, thus reducing or eliminating the unwanted image artefacts caused by the back-reflections in the resulting ocular image.

Example embodiments herein will now be explained in detail, with reference to the accompanying drawings.

Figure 1:
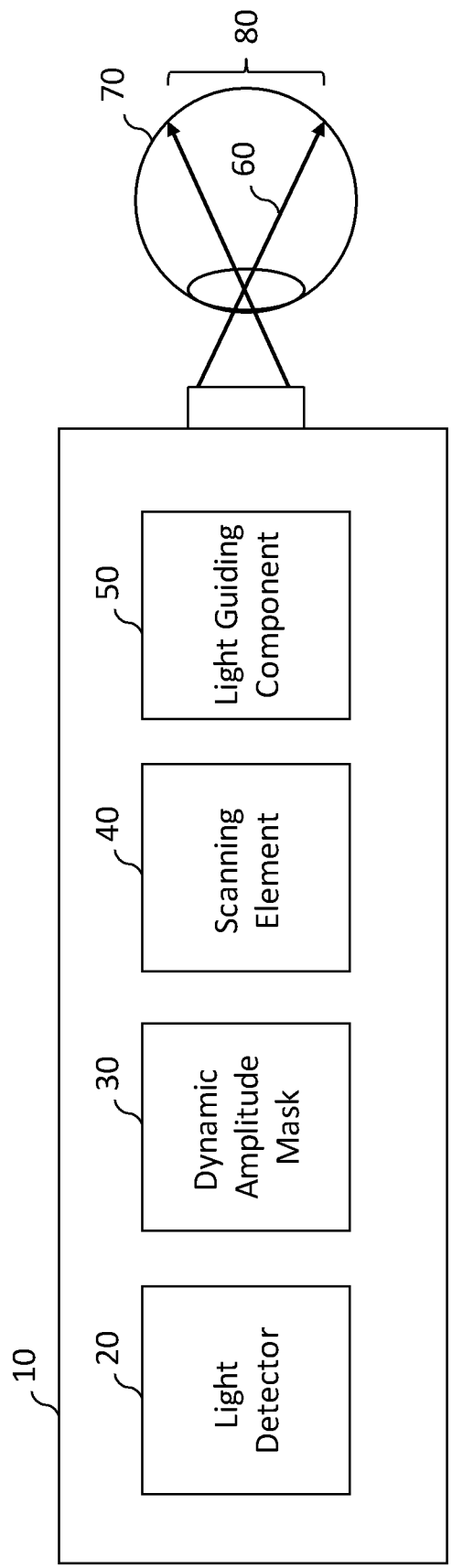
FIG. 1 is a schematic illustration of an ophthalmic imaging device according to a first example embodiment herein.

FIG. 1 is a diagram illustrating components of an ophthalmic imaging device 10 according to a first example embodiment herein. The ophthalmic imaging device 10 comprises a light guiding component 50, and at least one scanning element 40 which is operable to scan a light beam across the light guiding component 50 in one or more directions, such that a first portion of the light beam incident on the light guiding component 50 is guided by the light guiding component 50 to scan across a region 80 of the eye 70, and a second portion of the light beam incident on the light guiding component 50 is reflected back by the light guiding component 50 without having propagated through the light guiding component 50 to reach the eye 70.

The ophthalmic imaging device 10 further comprises a light detector 20, which is configured to detect light from the first portion of the light beam which has been reflected by the region 80 of the eye 70 and guided to the light detector 20 by the light guiding component 50.

Figure 4:
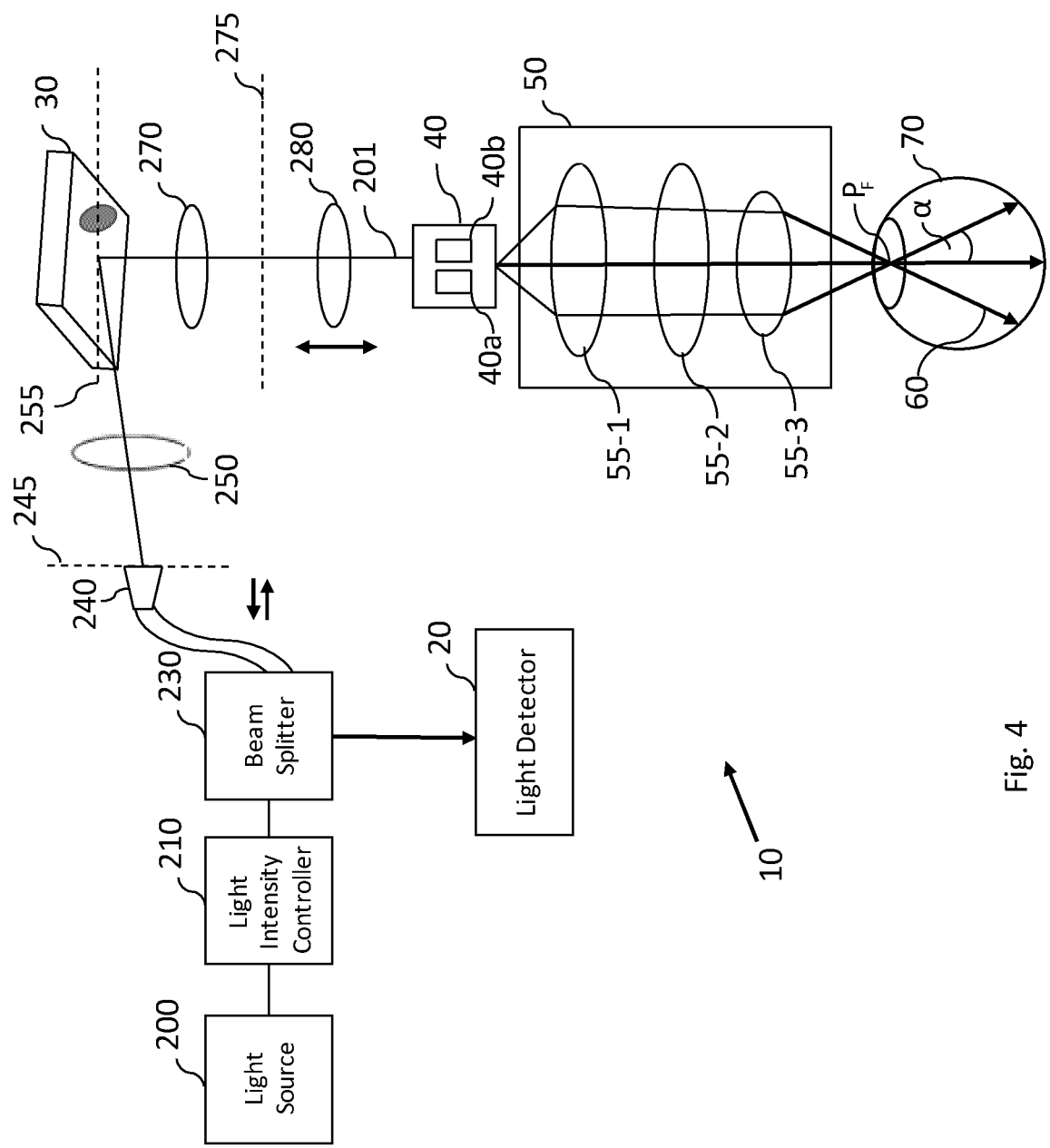
FIG. 4 is a schematic illustration of a first example implementation of the ophthalmic imaging device according to the first example embodiment.

The ophthalmic imaging device 10 further comprises a dynamic amplitude mask 30, which is located and oriented in the ophthalmic imaging device 10 so as to receive, from the light guiding component 50, the light from the first portion of the light beam which has been reflected by the region 80 of the eye 70. The dynamic amplitude mask 30 is also located and oriented in the ophthalmic imaging device 10 to receive, from the light guiding component 50, the light from the second portion of the light beam which has been reflected back by the light guiding component 50 (without having propagated through the light guiding component 50 to reach the eye 70) and is incident on the dynamic amplitude mask 30 with a spatial intensity distribution over a surface of the dynamic amplitude mask 30 that varies in a predetermined way with a scan angle, a, of the light beam scanned by the scanning element 40. The scan angle may be defined in a number of different ways. For example, the scan angle α may, as in the present example embodiment, be measured relative to a reference direction about a point on the scanning element 40 at which the light beam is reflected by the scanning element 40. The reference direction may, for example, be a direction along an optical path which, when followed by the light beam, leads the light beam to a central point of the scanned region 80 of the eye 70. It should be noted, however, that the scan angle α may otherwise be defined, for example relative to a reference direction (e.g. a conventional Z-axis of the ophthalmic imaging device 10), about a focal point $P_F$ of the ophthalmic imaging device 10 (as illustrated in FIG. 4, for example, which is discussed in more detail below).

The dynamic amplitude mask 30 has an unmasked portion, which is configured to allow the received light from the first portion of the light beam, which has been reflected by the region 80 of the eye 70, to propagate to the light detector 20 substantially unattenuated. The dynamic amplitude mask 30 also has a masked portion having a spatial distribution which varies in the predetermined way with the scan angle, such that the masked portion prevents at least some of the light from the second portion of the light beam reflected back by the light guiding component 50 from reaching the light detector 20 as the first portion of the light beam is scanned across the region 80 of the eye 70. The shape of the masked portion of the dynamic amplitude mask 30 may substantially follow an equal intensity contour in at least a part of the aforementioned spatial intensity distribution of the light reflected back by the light guiding component 50, for at least some (and preferably all) scan angles of the light beam that can be used in a scan performed by the ophthalmic imaging device 10. It should be noted that the masked portion includes all parts of the dynamic amplitude mask 30 which are configured to prevent at least some of the light from the second portion of the light beam reflected back by the light guiding component 50 from reaching the light detector 20. The distribution of the parts of the dynamic amplitude mask 30 forming the masked portion is, for any given scan angle, determined by the spatial intensity distribution in the plane of the dynamic amplitude mask of the light reflected back by the light guiding component 50 for that scan angle.

Figure 2A:
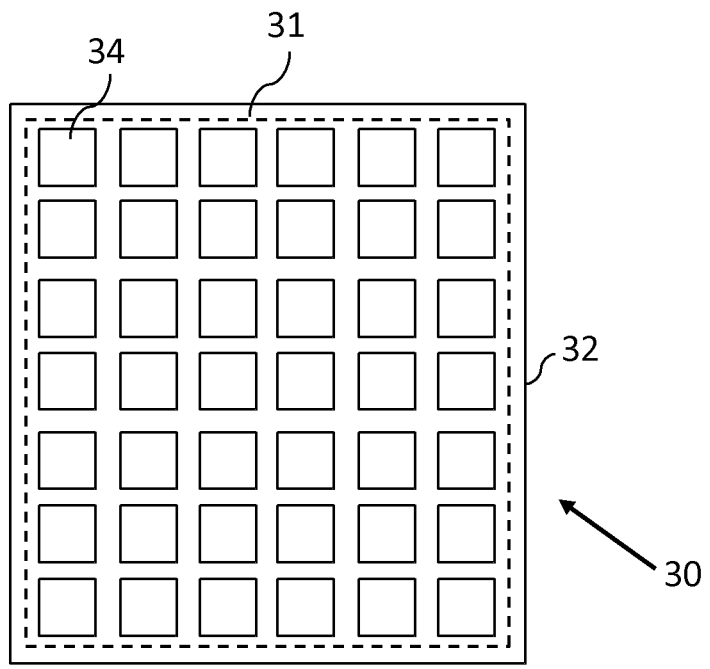
FIG. 2A illustrates a dynamic amplitude mask comprising an array of micromirrors according to the first example embodiment.
Figure 2B:
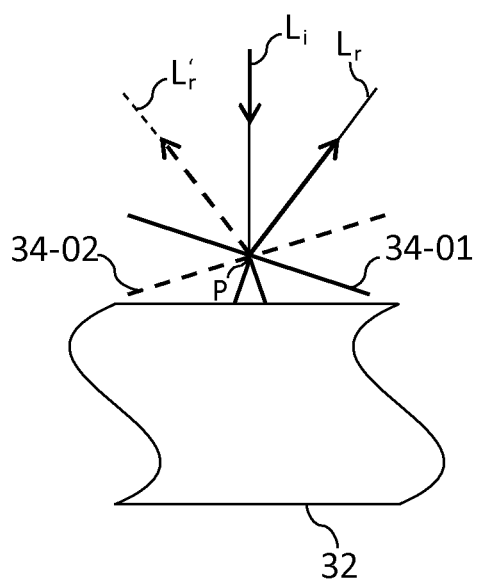
FIG. 2B illustrates two different orientations of a micromirror in the micromirror array of the dynamic amplitude mask illustrated in FIG. 2A.

By way of an example, the dynamic amplitude mask 30 may, as in the present example embodiment, comprise a micromirror array 31, as illustrated in FIG. 2A. In FIG. 2A, each micromirror 34 in the array 31 is mounted on a substrate 32 and is individually switchable between being in a first orientation and a second orientation. With reference to FIG. 2B, each micromirror 34 may change its orientation by rotating about a pivot P. As indicated by label 34-01 in FIG. 2B, when the micromirror 34 is oriented in the first orientation, the micromirror 34 reflects light which is incident upon the micromirror (and having come from the light guiding component 50), towards the light detector 20. In FIG. 2B, the light reflected towards the light detector 20 is labelled as $L_r$. On the other hand, when the micromirror 34 is orientated in the second orientation (as indicated by 34-02 in FIG. 2B), the micromirror 34 reflects the incident light away from the light detector 20, i.e. so that the reflected light, $L_r'$, in this case does not reach the light detector 20. Furthermore, the unmasked portion of the dynamic amplitude mask 30 may consist of (i.e. be composed entirely of) micromirrors of the array that are in the first orientation 34-01, and the masked portion of the dynamic amplitude mask 30 comprises micromirrors of the array that are in the second orientation 34-02 (and, optionally, some micromirrors in the first orientation 34-01, as described in more detail below). The orientation of each of the micromirrors of the dynamic amplitude mask 30 is controlled by a controller of the dynamic amplitude mask 30 (not shown), which provides drive signals for setting the micromirror orientations of the micromirrors 34.

Figure 3:
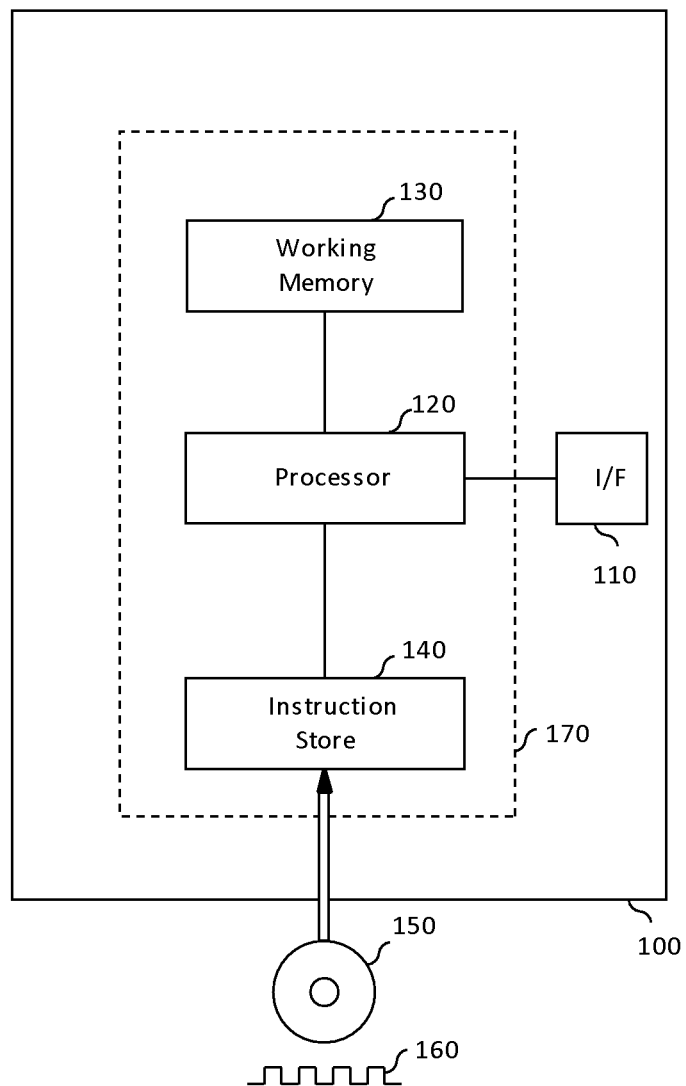
FIG. 3 shows an example of a hardware implementation of a controller forming part of the dynamic amplitude mask of the first example embodiment.

FIG. 3 shows an exemplary implementation of the controller of the dynamic amplitude mask 30 in FIG. 1, in programmable signal processing hardware. The hardware of FIG. 3 may also control one or more aspects of the operation of the ophthalmic imaging device 10, such as the driving one or more scanning elements so as to perform a scan of the light beam over the region 80 of the eye 70, and the generation of an ocular image from measurements performed by the light detector 20, for example. The signal processing apparatus shown in FIG. 3 comprises a communication interface (I/F) 110 for receiving information on one or more scan angles of the light beam scanned by the scanning element 40, and for transmitting control information to adjust the respective orientations of the micromirrors in the micromirror array. The signal processing apparatus 100 further comprises a processor (CPU) 120 for controlling the overall operation of the dynamic amplitude mask 30, a working memory 130 (e.g. a random access memory) and an instruction store 140 storing a computer program 190 comprising computer-readable instructions which, when executed by the processor 120, cause the processor 120 to perform the processing operations hereinafter described to control the arrangement of micromirror orientations in the dynamic amplitude mask 30. The instruction store 140 may comprise a ROM (e.g. in the form of an electrically-erasable programmable read-only memory (EEPROM) or flash memory) which is pre-loaded with the computer-readable instructions. Alternatively, the instruction store 140 may comprise a RAM or similar type of memory, and the computer-readable instructions can be input thereto from a computer program product, such as a computer-readable storage medium 150 such as a CD-ROM, etc. or a computer-readable signal 160 carrying the computer-readable instructions.

In the present example embodiment, the combination of the hardware components shown in FIG. 3, comprising the processor 120, the working memory 130 and the instruction store 140, is configured to implement the functionality of the controller of the dynamic amplitude mask 30, which will now be described in detail with reference to FIGS. 4 to 9.

FIG. 4 is a schematic showing an example implementation of the ophthalmic imaging device according to the first example embodiment The ophthalmic imaging device 10 may, as in the present example embodiment, be provided in the form of an SLO, which is configured to produce an image of the region 80 of the retina of the eye 70 (as an example of the scanned part of the eye 70) by using horizontal and vertical scanning mirrors (or a single XY scanning mirror that is rotatable about two (typically orthogonal) axes) to scan a focused laser beam across the region 80 in a raster pattern or the like, and using a light detector 20 to detect the light reflected from the scanned region 80 of the retina during the course of the scan. A pinhole may be placed in front of the light detector 20 for confocal detection.

The ophthalmic imaging device 10 further comprises a light source 200, such a laser, for generating light that is to form the scanning beam 201. The light source 200 may, for example, be configured to emit light having a wavelength in a range from 400 nm to 1100 nm. Light emitted from the light source 200 may, as in the present embodiment, be passed through a bandpass filter (not illustrated) such that only light having a specific wavelength range(s) is emitted towards the eye 70.

The one or more scanning elements 40 of the SLO is operable to scan the light beam 201 onto the light guiding component 50 and, in the present embodiment, takes the example form of a two-mirror scanner arrangement comprising an H-galvanometer mirror ("H-galvo") 40a and a V-galvanometer mirror ("V-galvo") 40b, which are provided in an optical arrangement that receives the light beam from the light source 200 and scans the light beam in a horizontal direction and a vertical direction onto the light guiding component 50, which subsequently guides the light onto the retina. The two galvanometer mirrors forming the scanning element 40 are rotated by respective motors under the control of a controller of the SLO (not shown) so as to vary the optical path of the light beam 201 to the light guiding component 50, and therefore vary the location on the retina that is illuminated and imaged using the light beam 201. In the present example embodiment, the scan angle of the light beam scanned onto the light guiding component 50 depends on the inclination angles ($\theta$, $\varphi$) of the H-galvanometer mirror 40a and the V-galvanometer mirror 40b, wherein angle $\theta$ is an inclination angle of the H-galvanometer mirror 40a and angle $\varphi$ is an inclination angle of the V-galvanometer mirror 40b. The inclination angles $\theta$ and $\varphi$ respectively indicate the degree of rotation of the H-galvanometer mirror 40a and the V-galvanometer mirror 40b about their respective axes of rotation. The H-galvanometer mirror 40a and the V-galvanometer mirror 40b may, for example, be provided in an arrangement as described in U.S. Pat. No. 7,959,290 B2, the contents of which are incorporated herein in their entirety. In this case, the H-galvanometer mirror 40a and the V-galvanometer mirror 40b may be arranged in the same way as the first scanning element (14) and the second scanning element (16) shown in FIG. 1 of this US patent, the arrangement including the described scan compensation means (18).

Figure 5:
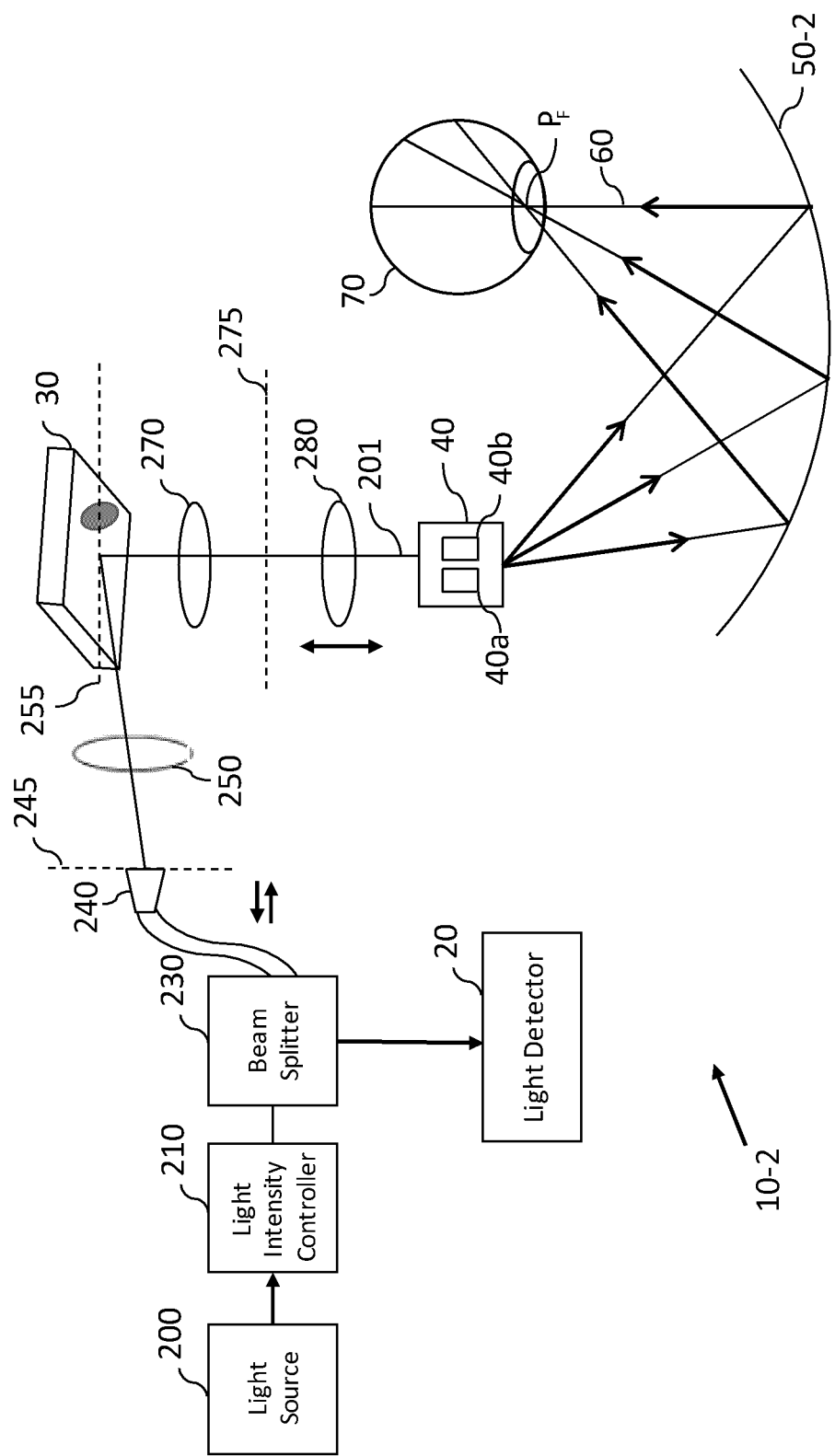
FIG. 5 is a schematic illustration of a second example implementation of the ophthalmic imaging device according to the first example embodiment.

The light guiding component 50 may, as in the present embodiment, take the form of a lens barrel comprising a set of convex lens 55-1 to 55-3, which is configured to guide the light beam 201 from the scanning element 40 to a point on the retina that depends on the inclination angles (θ, φ), and to guide light that is reflected by the retina back to the scanning element 40. However, the light guiding component 50 need not be lens-based, and may, for example, take the alternative form of one or more mirrors configured to guide the light beam 201 from the scanning element 40 onto the eye 70. FIG. 5 illustrates an example implementation of an ophthalmic imaging device 10-2, which employs a mirror-based light guiding component 50-2. As illustrated in FIG. 5, the light guiding component 50-2 may, as in the example of FIG. 5, take the form of an ellipsoidal mirror, with the scanning element 40 located at a first focal point of the mirror and the pupil of the eye 70 located at a second focal point, $P_F$, of the mirror during use of the ophthalmic imaging device 10-2. The ophthalmic imaging device 10-2 may thus employ an optical arrangement for wide-field imaging of the kind described in U.S. Pat. No. 5,815,242, for example, the contents of which are incorporated herein by reference in their entirety. Although the example of FIG. 5 employs an ellipsoidal mirror, the mirror can also take the form of an aspheric mirror or any mirror appropriately shaped to converge light beam to a part of the eye 70.

Referring again to the example embodiment in FIG. 4, the light guiding component 50 is incapable of transmitting substantially all of the light from the scanning element 40 to the eye 70 at all scan angles, and reflects a portion of the incident light back to the scanning element 40, wherein the portion reflected varies with the scan angle α of the light beam 201. Typically, in a lens-based imaging system of the kind illustrated in FIG. 4, strong back-reflections are obtained at specific values of the beam scan angle α. Similar problems also arise in many mirror-based imaging systems.

The ophthalmic imaging device 10 further comprises a light detector 20, which is configured to detect light that has been reflected by the retina and guided to the light detector 20 by the light guiding component 50.

The ophthalmic imaging device 10 also has a beam splitter 230, which serves to allow the light beam from the light source 200 to pass to the scanning element 40 whilst also guiding some of the light reflected from the retina to the light detector 20. An optical coupler 240 is connected to the beam splitter 230 and is configured to couple light from an image plane 255 of the ophthalmic imaging device 10 to the beam splitter 230.

The dynamic amplitude mask 30 may, as in the present embodiment, take the form of a digital micromirror device (DMD), for example. The DMD forming the dynamic amplitude mask 30 comprises an array of rotatable micromirrors, which are individually controllable by the controller of the dynamic amplitude mask 30 to switch from being in one of a first and a second, different orientation to the other of the first and second orientation. More specifically, the DMD may be configured to set each micromirror in the DMD either to a first orientation, in order to reflect light returned from the scanning element 40 towards the light detector 20, or to a second orientation such as to reflect incident light away from the light detector 20 and thus prevent light returned from the scanning element 40 from reaching the light detector 20. In this manner, the use of DMD allows binary amplitude modulation of the light received at each micromirror position on the DMD.

Figure 6A:
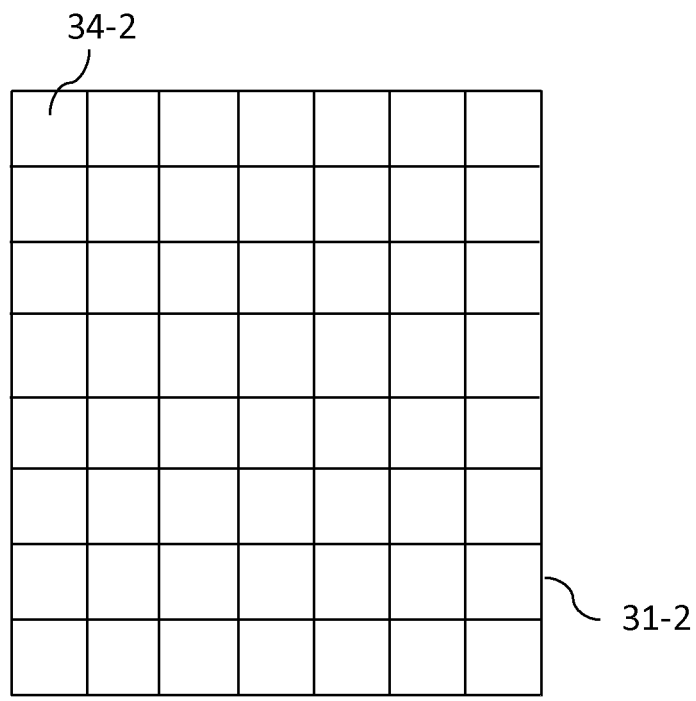
FIG. 6A illustrates a dynamic amplitude mask comprising an array of liquid crystal cells according to a variant of the first example embodiment.
Figure 6B:
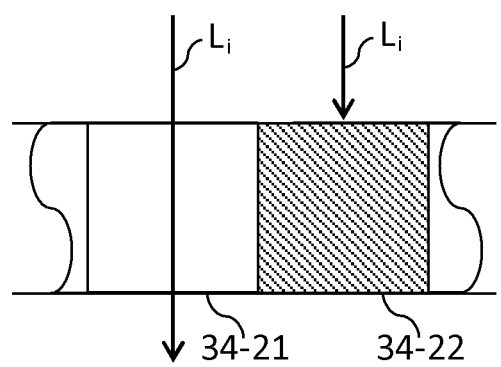
FIG. 6B illustrates a first liquid crystal cell in a first liquid crystal arranged to block incident light, and a second liquid crystal cell in a second liquid crystal phase arranged to transmit incident light.

It should be noted that the functionality of the dynamic amplitude mask 30 may be provided by any suitable type of spatial light modulator other than a DMD, such an array of liquid crystal cells, or an analog micromirror array, for example. Referring to FIG. 6A, in an alternative example embodiment, where the dynamic amplitude mask comprises an array 31-2 of liquid crystal cells, the liquid crystal in each liquid crystal cell 34-2 of the array 31-2 may be individually switchable between a first liquid crystal phase and a second liquid crystal phase. As shown in FIG. 6B, a liquid crystal cell 34-21 that is in the first liquid crystal phase transmits light $L_i$ incident thereon towards to the light detector 20. A liquid crystal cell 34-22 that is in the second liquid crystal phase, on the other hand, blocks incident light $L_i$, preventing it from being transmitted to the light detector 20. Furthermore, the unmasked portion of the dynamic amplitude mask 30 may consist of liquid crystal cells of the array 31-2 having liquid crystals in the first phase, while the masked portion of the dynamic amplitude mask 30 may comprise liquid crystal cells of the array having liquid crystals in the second phase.

Returning to the example embodiment illustrated in FIG. 4, the dynamic amplitude mask 30 is arranged in the ophthalmic imaging device 10 to receive, from the light guiding component 50, light reflected from the eye 70, as well as light reflected back by one or more optical surfaces of the light guiding component 50. As noted above, this reflected light is incident on the dynamic amplitude mask 30 with a spatial intensity distribution that varies as a function of the scan angle α of the light beam 201 scanning by the scanning element 40.

The dynamic amplitude mask 30 in the form of the DMD may, as in the present example embodiment, be placed in a Fourier plane 255 of ophthalmic imaging device 10, in an optical path between the scanning element 40 and the light detector 20, such that light reflected from the eye 70 is guided by the scanning element 40 to the light detector 20 via the dynamic amplitude mask 30. As the DMD is placed in the Fourier plane 255, the intensity distribution of light incident upon the DMD is indicative of the angular distribution of the intensity of the light received from light guiding component 50.

By way of an example, a convex lens 270 implements Fourier transform of the SLO light returned by the scanning element 40, while a convex lens 250 implements an inverse transform so that the plane 245 behind convex lens 250 is an image plane of the ophthalmic imaging device 10. The Fourier plane 255 of the returned light from the scanning element 40 is thus located between lenses 250 and 270, at a position that is one focal length from each of lenses 250 and 270. The convex lens 250 may, as in the present example embodiment, be placed at a distance of one focal length away from the optical coupler 240.

The ophthalmic imaging system 10 may, as in the present embodiment, further comprise a convex lens 280 for refocusing the light returned from the scanning element 40 in order to compensate for diffraction errors in the subject's eye 70. In the present example, the position of the convex lens 280 is controlled by a motor such that the light returned from the eye 70 is focused onto an intermediate image plane positioned at 275.

Although the dynamic amplitude mask 30 is located in a Fourier plane 255 of the ophthalmic imaging device 10 in the present example embodiment, it should be noted that the dynamic amplitude mask 30 may alternatively be placed in an image plane of the ophthalmic imaging device 10, such as for example, the plane at 275. As a further alternative, the dynamic amplitude mask 30 may be placed in a plane which is between the image plane and the Fourier plane of the ophthalmic imaging device 10.

Figure 7:
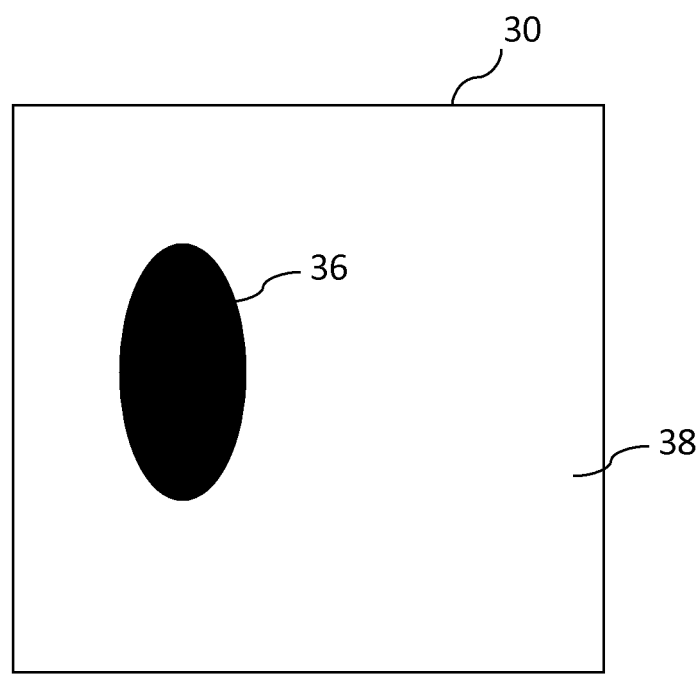
FIG. 7 illustrates an example of a masked portion and an unmasked portion of the dynamic amplitude mask of the first example embodiment herein.

The dynamic amplitude mask 30 has an unmasked portion which is configured to allow light reflected from the eye 70 (and guided to the mask 30 by the light guiding component 50) to propagate to the light detector 20, as well as a masked portion that is configured to prevent at least some of the back-reflected light (i.e. light from the scanning element 40 that has been reflected back by the light guiding component 50 without having been incident on the eye 70) from reaching the light detector 20. The masked portion of the dynamic amplitude mask 30 may, as in the present embodiment, consist of micromirrors of the DMD that are set to the first orientation as defined above, while the unmasked portion consists of the micromirrors in the DMD which are set to the second orientation as defined above. FIG. 7 provides an example schematic illustration of a dynamic amplitude mask 30 comprising a masked portion 36 and an unmasked portion 38. It should be noted that, although FIG. 7 illustrates the masked portion 36 to be formed by a single region of the mask 30, the masked portion 36 may alternatively be formed by a plurality of isolated regions on the dynamic amplitude mask 30.

Moreover, although the dynamic amplitude mask 30 of the present example embodiment is formed by spatially discrete masking elements, as described above, the dynamic amplitude mask 30 may alternatively be configured to provide optical masking that is continuously variable across a surface of the mask, for example by employing a continuously deformable reflective surface. Furthermore, the dynamic amplitude mask 30 need not perform a binary modulation of light as described above and may, in some example embodiments, modulate the intensity of the received light to provide intermediate output light intensity levels that are between a maximum intensity level (corresponding to the light passing from the mask 30 to the light detector 20 unattenuated) and a minimum intensity level (corresponding to the light being completely masked (or blocked) by the dynamic amplitude mask 30, so that the light detector 20 detects a value corresponding to zero light intensity).

The controller (not shown) of the dynamic amplitude mask 30 mentioned above is configured to vary the spatial distribution of the masked portion 36 as a function of the scan angle $\alpha$ of the light beam 201 scanned by the scanning element 40, so that the shape of the masked portion 36 follows the spatial intensity distribution of the back-reflected light from the light guiding component 50 at the dynamic amplitude mask 30 as the scan angle $\alpha$ of the light beam 201 varies during the course of a scan. The dynamic amplitude mask 30 is thus configured to at least partially reduce the intensity of the unwanted back-reflected light for all values of the scan angle $\alpha$.

The dynamic amplitude mask 30 may, as in the present example embodiment, be configured to receive information indicative of the scan angle $\alpha$ of the light beam 201 scanned by the scanning element 40 (for example, signals that are indicative of the inclination angles $\theta$ and $\varphi$, such as drive signals generated by the controller of the SLO for setting the orientations of the H-galvo 40$a$ and V-galvo 40$b$), and use the received information to determine which of the micromirrors 34 in the micromirror array 31 should be set to the first orientation so as to form the unmasked portion 38, and which of the micromirrors 34 should be set to the second orientation to form at least a part of the masked portion 36. This determination may, as in the present example embodiment, be based on pre-stored mask configuration information which indicates respective orientations of the micromirrors of the dynamic amplitude mask 30 that are to be set for each scan angle range of a plurality of scan angle ranges. The mask configuration information may be stored in any suitable form, such as a look-up table, for example. Furthermore, the mask configuration information may, as in the present embodiment, be obtained in advance through a calibration process, as described below.

The mask configuration information for each scan angle range may be determined in advance based on a characterization of the spatial intensity distribution of the back-reflected light over a surface of the dynamic amplitude mask 30. The spatial intensity distribution of the back-reflected light on the dynamic amplitude mask 30 may, for example, be characterised by controlling the ophthalmic imaging device 10 to perform an imaging scan on a substantially non-reflective imaging target (in place of eye 70) or with no imaging target being present, so that little or no light other than the back-reflected light is returned by the light guiding component 50. In this case, a photodetector array (not shown) can be arranged in the ophthalmic imaging device 10 in place of the dynamic amplitude mask 30 in the calibration process to measure the back-reflected light for a number of different scan angles. For example, in an example embodiment in which the dynamic amplitude mask 30 is placed in a Fourier plane (e.g., plane 255) of the ophthalmic imaging device 10 for normal operation of the device 10, as in the present example embodiment, the back-reflection intensity distribution may be characterised based on a calibration process wherein a photodetector array is placed in the same Fourier plane and used to acquire a "reflection image", which provides an indication of the angular intensity distribution of the back-reflected light. It should be noted that, in alternative embodiments where the dynamic amplitude mask 30 is placed in an image plane of the ophthalmic imaging device 10 for normal operation of the device 10, a back-reflection intensity distribution may similarly be characterised based on a calibration process using the photodetector array placed in the same image plane (in place of the dynamic amplitude mask 30) in order to measure the spatial intensity distribution of the back-reflected light across this plane for a number of different scan angles.

The photodetector array (not shown) used to generate the reflection image may have a detection surface that is substantially of the same size as a light-receiving surface of the dynamic amplitude mask 30, and may have a photodetector array density such that each photodetector location can be mapped to a corresponding element of the dynamic amplitude mask 30, for example, to a corresponding micromirror 34 on the micromirror array 31 forming the dynamic amplitude mask 30 of the present example embodiment. The photodetector array may alternatively have a detection surface that is larger than that of the light-receiving surface of the dynamic amplitude mask 30, and a different photodetector array density, and the mapping between photodetector locations and corresponding elements of the dynamic amplitude mask 30 may be determined by interpolation, for example.

During the calibration process, the photodetector array may be controlled by the controller of the SLO (or a dedicated computer connected to the photodetector array during the calibration process, for example) to record, for each of a plurality of scan angles, a spatial intensity distribution of light incident on the photodetector array from the light guiding component 50 when the ophthalmic imaging device 10 images a test imaging target with a very low (ideally zero) reflectivity. The intensity of the light detected at all photodetector locations across the photodetector array is recorded by the SLO controller to generate a reflection image for each scan angle α. Pixel positions where light detected at the array (resulting from the device imaging the test image) exhibits an intensity value above a predetermined threshold may be identified and recorded to indicate the positions of the array which detect a significant level of the back-reflection. As each photodetector location on the photodetector array corresponds to a respective micromirror on the dynamic amplitude mask 30 in the present example, the regions of the photodetector array experiencing a significantly high intensity of the back-reflected light (i.e. above a predetermined threshold level) may be used to determine the masked region of the dynamic amplitude mask 30.

For example, in the present example embodiment, after obtaining the reflection image for a given scan angle, the photodetectors in the photodetector array which have measured an intensity value above the predetermined threshold are mapped to micromirrors 34 of the micromirror array 31 that are correspondingly located on the dynamic amplitude mask 30, and which are to be set to the second orientation so as to form the masked portion for that scan angle α. Information identifying these micromirrors may be stored as mask configuration information, in association with the selected scan angle in a memory unit (e.g. the instruction store 140) within the ophthalmic imaging device 10. During normal operation of the ophthalmic imaging device 10, the dynamic amplitude mask 30 may, for each planned scan angle to be used when imaging a corresponding point in the region 80 of the eye 70, retrieve (from the memory unit) the mask configuration information associated with a scan angle used during calibration which is closest to the planned scan angle, and use the retrieved mask configuration information to configure the dynamic amplitude mask 30 so as to prevent back-reflected light generated for that scan angle from reaching the detector 20 (or to at least reduce the intensity of the back-reflected light).

The above-described calibration process is performed for a plurality of scan angles, and respective mask configuration information is stored (in the memory unit) for each of the plurality of scan angles. For each planned scan angle that is to be used by the ophthalmic imaging system 10 whilst performing a scan, the mask configuration information stored in association with the closest scan angle used during calibration may be retrieved and used to set the configuration of the dynamic amplitude mask 30.

FIGS. 8A and 8B illustrate examples of look-up tables storing mask configuration information obtained during the calibration procedure described above, which can be used by the ophthalmic imaging device 10 to determine micromirror orientations to be used during the course of a scan. The example look-up tables may be stored in, for example, the memory unit.

FIG. 8A illustrates an example look-up table storing mask configuration information obtained during calibration for an inclination angle θ of the H-galvo mirror 40a of the scanning element 40 of 10°, and an inclination angle φ of the V-galvo mirror 40b of 10°. The look-up table in FIG. 8A stores the mask configuration information in the form of a two-dimensional array of binary bit values, each of the binary bit values representing either the first orientation or the second orientation of a correspondingly located micromirror in the micromirror array. Bit value "1" in the table indicates that the micromirror 34 is to be set to the first orientation described above, and bit value "0" indicates that the micromirror 34 is to be set to the second orientation. FIG. 8B illustrates another example look-up table storing mask configuration information for a second set of scan angles, namely θ=20° and φ=20°. Of course, the example look-up tables shown in FIGS. 8A and 8B are for purposes of illustration only, and the scope of the invention is not necessarily limited thereto.

Each micromirror 34 in the dynamic amplitude mask 30 is assigned a (x, y) coordinate and corresponds to an entry in the table. Accordingly, the look-up tables in the illustrative examples of FIGS. 8A and 8B provide mask configuration information for a dynamic amplitude mask having a two-dimensional array of 16 micromirrors, although in other example embodiments herein the look-up tables may more generally store mask configuration for a dynamic amplitude mask having a smaller or larger number of micromirrors in its micromirror array. In some practical implementations of the ophthalmic imaging device 10, the look-up table may have hundreds or thousands of entries, for example.

In some example embodiments, the masked portion of the dynamic amplitude mask 30 may comprise an interleaved arrangement of micromirrors 34 in the first orientation and micromirrors in the second orientation. In such example embodiments, the dynamic amplitude mask 30 may be configured to receive a ratio-setting signal generated based on a user input (via an input device such as a keyboard or touchpad connected to the controller) and set, in accordance with the received ratio-setting signal, a ratio of the number of micromirrors 34 in the first orientation in the masked portion to the number of micromirrors 34 in the second orientation in the masked portion.

Figure 9:
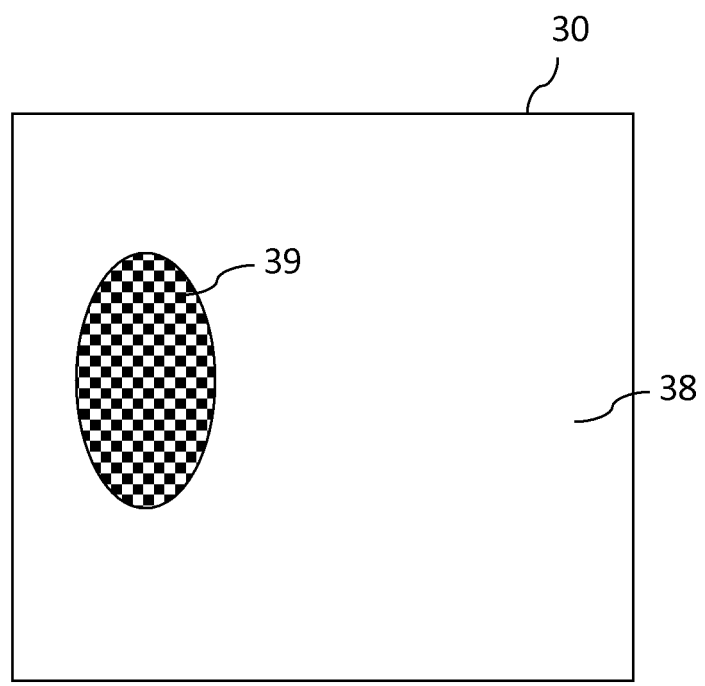
FIG. 9 illustrates an example of an interleaved arrangement of micromirrors in a masked portion of the dynamic amplitude mask according to the first example embodiment herein.

FIG. 9 illustrates an example of a dynamic amplitude mask 30 having an unmasked portion 38 and a masked portion 39 that comprises an interleaved arrangement of micromirrors 34 in the first and second orientations, where the white squares in the illustrated checkerboard pattern in the masked portion 39 represent micromirrors in the first orientation while the black squares represent micromirrors in the second orientation. In the example of FIG. 9, the dynamic amplitude mask 30 is configured in accordance with a ratio-setting signal indicating a ratio of 50%, so that half of the micromirrors 34 within the masked portion 39 are set to the second orientation, with the remaining micromirrors 34 in the masked portion 39 being in the first orientation. By adjusting the ratio of the number of micromirrors 34 in the first orientation to the number of micromirrors 34 in the second orientation in the masked portion of the dynamic amplitude mask 30, the intensity of the light detected by the light detector 20 can be adjusted to obtain a satisfactory trade-off between SNR of the detected signal (reflection image) and the effectiveness of the back-reflection suppression.

In some example embodiments, where the dynamic amplitude mask 30 takes the alternative form of a liquid crystal cell array, the masked portion of the dynamic amplitude mask 30 may similarly comprise an interleaved arrangement of liquid crystal cells in the first phase and liquid crystal cells in the second phase. In such embodiments, the dynamic amplitude mask 30 may likewise be configured to receive a ratio-setting signal generated on the basis of a user input as described above and set, in accordance with the received ratio-setting signal, a ratio of the number of liquid crystal cells in the first phase in the masked portion of the dynamic amplitude mask 30 to the number of liquid crystal cells in the second phase in the masked portion of the dynamic amplitude mask 30.

It should be noted that, in example embodiments such as the one illustrated in FIG. 4, the dynamic amplitude mask 30 is preferably arranged in the ophthalmic imaging device 10 so as to mask not only the light that has travelled to the mask 30 from the eye 70 via the light guiding component 50 and the scanning element 40 but also the light travelling in the opposite direction, from the light source 200 towards the eye 70. In this kind of optical arrangement, the dynamic amplitude mask 30 may, in addition to suppressing the back-reflected light, also vary the intensity of the light entering the eye 70 as the scan angle α and thus the configuration of the mask 30 varies during the course of a scan being performed by the ophthalmic imaging device 10. The fluctuation of the intensity of the light beam entering the eye 70 may cause artefacts in the acquired ocular image.

To address the foregoing, the ophthalmic imaging device 10 may, as in the present example embodiment, further comprise a light intensity controller 210, which is configured to control the intensity of the light received by the dynamic amplitude mask 30, which is to form the light beam 210 scanned across the light guiding component 50 by the scanning element 40, as a function of the scan angle α, so that the intensity of the light beam 201 scanned across the light guiding component 50 by the scanning element 40 is substantially independent of the scan angle α.

The light intensity controller 210 may, as in the present example embodiment, comprise a variable optical attenuator (not shown in FIG. 4), which is configured to attenuate light (from light source 200) that is to be received by the dynamic amplitude mask 30 and form the light beam scanned across the light guiding component 50 by the scanning element 40. The light intensity controller 210 may be configured to control the variable optical attenuator to vary the attenuation of the light as a function of the scan angle such that the intensity of the light beam scanned across the light guiding component 50 by the scanning element 40 is substantially independent of the scan angle. The level of attenuation performed by the variable optical attenuator (not shown) may be selected based on a pre-characterization of a power fluctuation of the light launched into the eye 70 for each of a number of different scan angles. This pre-characterization may be done by measuring the intensity of the light beam output from the ophthalmic imaging device 10 for each of the scan angles. Alternatively, the light intensity controller 210 may, as in the present embodiment, be configured to control the variable optical attenuator (not shown) to vary the attenuation of the light by using the mask configuration information for each scan angle. For example, in some embodiments, the light intensity controller 210 may control the variable optical attenuator to vary its attenuation based the variation of the micromirror orientation ratio with scan angle that has been discussed above (e.g., and corresponding information from a look-up table). More generally, as the fluctuation of the intensity of the light beam scanned across the eye 70 is directly related to changes in the area of the masked portion 32 on the dynamic amplitude mask 30, any information that is indicative of a variation of the area of the masked portion with the scan angle may be used by the controller 210 to set the required level of attenuation of the attenuator as a function of scan angle.

Embodiment 2

In the example embodiments described above, a single dynamic amplitude mask 30 is provided in the ophthalmic imaging device 10, for example in a Fourier plane (e.g., 255) or an image plane (e.g., 275) of the ophthalmic imaging device 10. However, the ophthalmic imaging device may comprise more than one dynamic amplitude mask 30 and may, as in the present example embodiment, comprise a first dynamic amplitude mask that is located in a Fourier plane of the ophthalmic imaging device (same as in the first example embodiment) and a second dynamic amplitude mask that is located in an image plane of the ophthalmic imaging device. The second dynamic amplitude mask may comprise a second unmasked portion and a second masked portion, wherein the second masked portion also has a spatial distribution that is configured to vary as a function of the scan angle of the light beam scanned by the scanning element 40.

Thus, in the second example embodiment, which is a variant of the example embodiment described above with reference to FIG. 4, the first dynamic amplitude mask is placed in the Fourier plane 255, and the second dynamic amplitude mask is placed in the image plane 275. The first dynamic amplitude mask is thus arranged to perform, based on the scan angle, spatial light modulation of the light reflected from the light guiding component 50 in the Fourier plane. The second dynamic amplitude mask is configured to perform, based on the scan angle, spatial light modulation of the light reflected from the light guiding component 50 in the image plane.

In the second example embodiment, although both the first dynamic amplitude mask and the second dynamic amplitude mask are configured to vary the spatial distributions of their respective masked portions based on the scan angle, it should be noted that, for any scan angle, the first dynamic amplitude mask may be configured to have a masked portion that has a different spatial distribution than that of the masked portion of the second dynamic amplitude mask, as the spatial distribution of reflected light incident on the two dynamic amplitude masks may be different. A calibration process similar to that described above with reference to the first example embodiment may be used to obtain the mask configuration information of the second dynamic amplitude mask.

In other respects, the present example embodiment is the same as the first example embodiment, and the variations and modifications to the first example embodiment described above are applicable to the present embodiment.

Embodiment 3

In a third example embodiment, the masked and unmasked portions of the dynamic amplitude mask described in the first example embodiment are provided in a first region of a plane (wherein those portions are referred to as a first masked portion and a first unmasked portion, respectively), and the dynamic amplitude mask further comprises a second masked portion and a second unmasked portion, which are provided in a second region of the same plane, the second region being distinct or separate from the first region. Moreover, the first region of the plane coincides with a Fourier plane of the ophthalmic imaging device, and the second region of the plane coincides with an image plane of the ophthalmic imaging device.

In addition, the second unmasked portion is configured to allow light from the first portion of the light beam, which has been reflected by the region 80 of the eye 70 and has passed through the (first) unmasked portion in the first region of the dynamic amplitude mask, to propagate to the light detector 20. Furthermore, the second masked portion has a spatial distribution which is configured to vary as a function as the scan angle. In particular, the spatial distribution of the second masked portion is configured to vary such that the second masked portion prevents at least some of the light from the second portion of the light beam reflected back by the light guiding component 50, and which has passed through the (first) unmasked portion of the dynamic amplitude mask in the first region, from reaching the light detector 20, as the first portion of the light beam is scanned across the region 80 of the eye 70.

Figure 10:
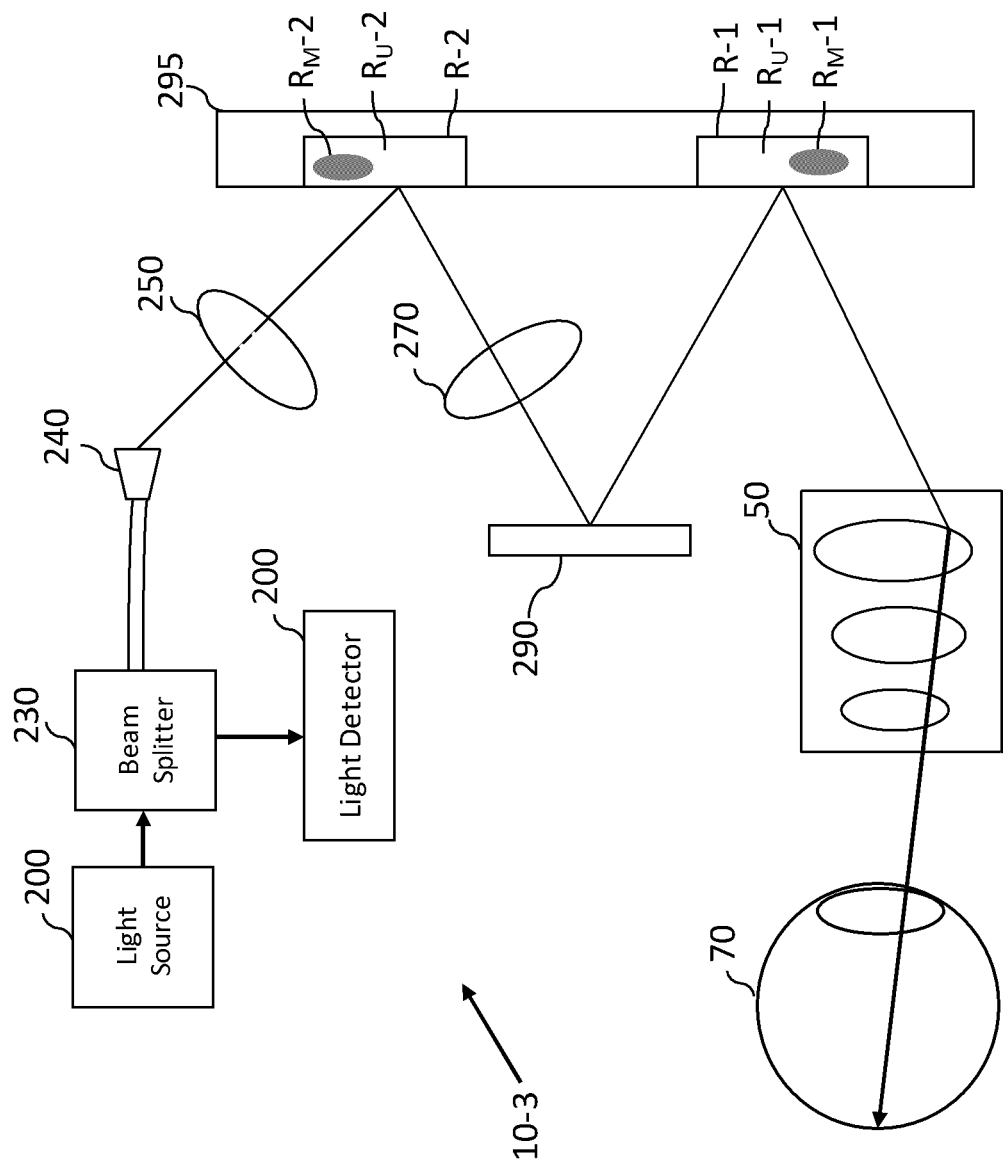
FIG. 10 illustrates an example implementation of an ophthalmic imaging device according to a third example embodiment herein.

FIG. 10 is a schematic illustration of an ophthalmic imaging device 10-3 in accordance with the third example embodiment. In FIG. 10, a dynamic amplitude mask 295 comprises a first region R-1 that coincides with an image plane of the ophthalmic imaging device 10-3. The first region R-1 comprises a first masked portion RM-1 and a first unmasked portion Pu-1. The dynamic amplitude mask 295 further comprises a second region R-2 that coincides with a Fourier plane of the ophthalmic imaging device 10-3. The second region R-2 comprises a second masked portion RM-2 and a second unmasked portion Ru-2. As illustrated in FIG. 10, the first region R-1 and the second region R-2 are located in the same plane and are separate from one another. Other components of the ophthalmic imaging device 10-3 illustrated in FIG. 10 having the same reference numerals as those shown in the first example embodiment of FIG. 4, function in the same way as the corresponding components of the first example embodiment illustrated in FIG. 4. Besides the different implementation of the dynamic amplitude mask 295, the only difference is that in FIG. 10 there is a re-arrangement of converging lenses 250 and 270, and a mirror 290 is provided that serves to guide light between the first region R-1 and the second region R-2. This rearrangement allows a Fourier plane of the ophthalmic imaging device 10-3 and the imaging plane of the ophthalmic imaging device 10-3 to be co-planar, in the example embodiment shown in FIG. 10.

In other respects, the present example embodiment is the same as the first example embodiment, and the variations and modifications to the first example embodiment described above are applicable to the present embodiment.

Embodiment 4

The ophthalmic imaging devices of the example embodiments described above are each provided with at least one dynamic amplitude mask 30, 295 for physically masking off the light returned by the light guiding component 50, in order to reduce the unwanted reflection in the image generated by the light detector 20, 200. The ophthalmic imaging device of the fourth example embodiment, on the other hand, is configured to perform the masking in a digital domain, specifically by processing images acquired during the course of a scan to reduce unwanted reflections therein. The present example embodiment differs from the first example embodiment by having, in place of the light detector 20 and the dynamic amplitude mask 30 as a physical component, a photodetector and an image processor configured to implement a digital mask which processes a detected image and digitally removes unwanted reflections. However, in common with the foregoing example embodiments, the present example embodiment also makes use of information indicating how the intensity distribution of reflections from the light guiding component 50 varies with the scan angle. In particular, due the angle-dependent nature of the reflected light, the digital mask is adapted to perform the digital masking dynamically based on the scan angle of the light beam scanned by the scanning element.

Figure 11:
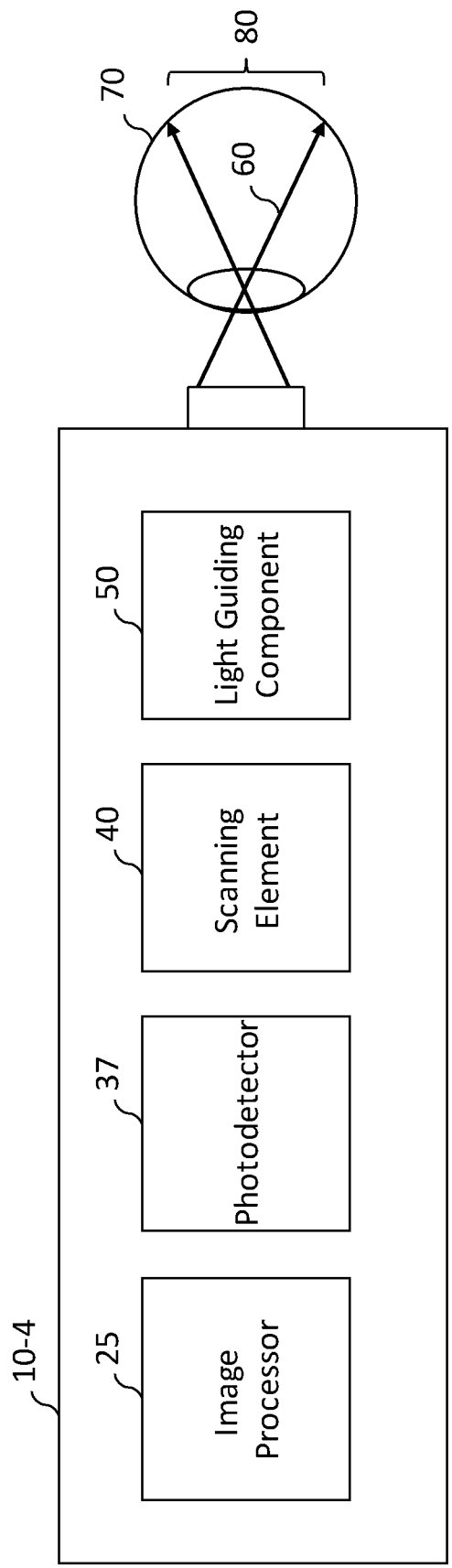
FIG. 11 is a schematic illustration of an ophthalmic imaging device according to a fourth example embodiment herein.

FIG. 11 illustrates an ophthalmic imaging device 10-4 for imaging the eye 70 according to the fourth example embodiment. The ophthalmic imaging device 10-4 comprises a light guiding component 50 and a scanning element 40, which are the same as in the first embodiment. That is, the scanning element 40 is operable to scan a light beam across the light guiding component 50 such that a first portion of the light beam incident on the light guiding component 50 is guided by the light guiding component 50 to scan across a region of the eye 70, and a second portion of the light beam incident on the light guiding component 50 is reflected back by the light guiding component 50.

The ophthalmic imaging device 10-4 further comprises a photodetector 37 having a light-detection surface. The photodetector 37 is arranged in the ophthalmic imaging device 10-4 so as to detect a spatial light intensity distribution of light that is incident on the light-detection surface, the incident light comprising the light from the first portion of the light beam which has been reflected by the region 80 of the eye 70 and guided to the photodetector 37 by the light guiding component 50, and the light from the second portion of the light beam which has been reflected back by the light guiding component 50 and is incident on the photodetector 37 with a spatial intensity distribution over the light detection surface that varies as a function of a scan angle of the light beam scanned by the scanning element 40.

By way of an example, the photodetector 37 may, as in the present embodiment, be provided in the form of a complementary metal-oxide-semiconductor (CMOS) image sensor. However, the photodetector 37 may alternatively take the form of a charge-coupled device (CCD) image sensor, for example, or any other device that is capable of recording a spatial intensity distribution of light incident thereon. Furthermore, in the present example embodiment, the photodetector 37 is placed in an image plane of the ophthalmic imaging device 10-4, although the photodetector 37 can alternatively be placed in the Fourier plane of the ophthalmic imaging device 10-4, or in another plane which is located between the image plane and the Fourier plane.

The ophthalmic imaging device 10-4 further comprises an image processor 25, which is configured to process data generated by the photodetector 37, which is indicative of the spatial light intensity distribution detected by the photodetector 37 over a detection surface thereof, specifically by applying a digital mask to the data indicative of the spatial light intensity distribution so as to reduce values of the detected light intensity in a masked portion of the detected spatial light intensity distribution that has been masked by the digital mask, and to generate image data based on the processed light intensity distribution. For example, where the data generated by the photodetector 37 can be represented as a two-dimensional array of pixel values, each pixel value being indicative of the light intensity measured by the photodetector 37 at a respective location on the detection surface corresponding to the location of the pixel, the digital mask may comprise a correspondingly sized array of mask values, the image processor 25 being configured to process the data acquired by the photodetector 37 by multiplying each pixel in the two-dimensional array of pixel values by the mask value which is correspondingly located in the digital mask. By way of an example, each mask value may be "1" or "0", so that a masked portion of the detected spatial light intensity distribution consists of zeros, while the remaining unmasked portion of the detected spatial light intensity distribution consists of the unchanged intensity values as detected by the photodetector 37. The masked portion has a spatial distribution of zeros which is configured to vary as a function of the scan angle so as to substantially eliminate a contribution of the light from the second portion of the light beam which has been reflected back by the light guiding component 50 to the image data generated by the image processor 25 as the first portion of the light beam is scanned across the region 80 of the eye 70.

It should be noted, however, that the mask values, with which the correspondingly located pixels in the two-dimensional array of pixel values generated by the photodetector 37 are multiplied in the masked portion of the spatial light intensity distribution, need not be "0", and could alternatively take any intermediate value between 1 and 0 so that the masked portion has a spatial distribution of the weighted values which is configured to vary as a function of the scan angle so as to reduce to some degree (e.g. by a predefined percentage) a contribution of the light from the second portion of the light beam which has been reflected back by the light guiding component 50 to the image data generated by the image processor 25 as the first portion of the light beam is scanned across the region 80 of the eye 70.

The image processor of the fourth example embodiment may be implemented using the programmable signal processing hardware illustrated in FIG. 3 and previously described in relation to the implementation of a controller for the dynamic amplitude mask 30 of foregoing example embodiments.

As with the dynamic amplitude mask 30 of the first, second and third example embodiment, the digital mask of the present example embodiment is dynamically configured for different scan angles of the light beam scanned by the scanning element 40. More specifically, the mask values used to perform the digital masking may vary depending on the scan angle used, such that a different region of the detected spatial light distribution is masked for each different scan angle. To determine an appropriate digital mask for each scan angle employed by the ophthalmic imaging device 10-4, a similar calibration process as described in relation to the first, second and third example embodiments may be used. More specifically, the spatial intensity distribution of the back-reflected light can be characterised for each scan angle by performing a scan on a substantially non-reflective imaging target or with no imaging target being present. Based on spatial light distribution of the back-reflected light on the photodetector 37, a set of mask values corresponding to each digital mask can be set for each scan angle and stored in a memory of the ophthalmic imaging device.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized (and navigated) in ways other than those shown in the accompanying figures.

Software embodiments of the examples presented herein may be provided as, a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment (and can form a memory or store). The program or instructions on the non-transitory machine-accessible medium, machine-readable medium, memory, instruction store, or computer-readable storage device or medium, may be used to program a computer system or other electronic device. The machine- or computer-readable device/medium, memory, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable medium", "machine-accessible medium", "machine-readable medium", "memory", "instruction store", "computer-readable storage medium", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, memory, instruction store(s), or storage device(s), having instructions stored thereon or therein which can be used to control, or cause, a computer or computer processor to perform any of the procedures of the example embodiments described herein. The storage medium/memory/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, memory, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that any procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Having now described some illustrative embodiments and embodiments, it is apparent that the foregoing is illustrative and not limiting, having been presented by way of example.

The devices and apparatus described herein may be embodied in other specific forms without departing from the characteristics thereof. The foregoing embodiments are illustrative rather than limiting of the described systems and methods. Scope of the optical systems and apparatuses described herein is thus indicated by the appended claims, rather than the foregoing description, and changes that come within the meaning and range of equivalence of the claims are embraced therein.

The invention claimed is:

1. An ophthalmic imaging device for imaging an eye, comprising:
    a scanning element arranged in a light path to scan at least a region of the eye with a light beam propagating along the light path;
    a light guiding component arranged in the light path, and through which at least a first portion of the light beam is guided to scan across the region of the eye and then reflected by the region back in the light path by way of the light guiding component, wherein a second portion of the light beam is reflected back into the light path by the light guiding component without having scanned the eye;
    a light detector arranged to detect the first portion of the light beam after it has been reflected back in the light path by way of the light guiding component; and
    a dynamic amplitude mask arranged in the light path to receive the first portion of the light beam reflected back in the light path by way of the light guiding component, and the second portion of the light beam which has been reflected back into the light path by the guiding component and which is incident on the dynamic amplitude mask with a spatial intensity distribution that varies as a function of a scan angle of the light beam scanned by the scanning element,
    wherein the scanning element is interposed between the dynamic amplitude mask and the light guiding component in the light path, and
    wherein the dynamic amplitude mask comprises an unmasked portion configured to allow the first portion of the light beam, which has been reflected by the region of the eye, to propagate to the light detector, and a masked portion having a spatial distribution which is configured to vary as a function of the scan angle such that the masked portion prevents at least some of the second portion of the light beam reflected back by the light guiding component from reaching the light detector as the first portion of the light beam is scanned across the region of the eye.

2. The ophthalmic imaging device according to claim 1, wherein light guiding component comprises one of:
    one or more lenses configured to guide the first portion of the light beam to scan across the region of the eye; or
    a mirror having a shape configured to guide the first portion of the light beam from the scanning element to a pupil of the eye, the scanning element being located at a first focal point of the mirror and a pupil of the eye being located at a second focal point ($P_F$) of the mirror during use of the ophthalmic imaging device.

3. The ophthalmic imaging device according to claim 1, wherein the dynamic amplitude mask comprises an array of micromirrors, each micromirror in the array being individually switchable between a first orientation, in which the micromirror reflects light incident thereon towards to the light detector, and a second orientation, in which the micromirror reflects light incident thereon away from the light detector, and wherein the unmasked portion of the dynamic amplitude mask consists of micromirrors of the array that are in the first orientation, and the masked portion of the dynamic amplitude mask comprises at least some micromirrors of the array that are in the second orientation.

4. The ophthalmic imaging device according to claim 3, wherein
    the masked portion of the dynamic amplitude mask comprises an interleaved arrangement of micromirrors in the first orientation and micromirrors in the second orientation, and
    the dynamic amplitude mask is configured to receive a ratio-setting signal and set, in accordance with the received ratio-setting signal, a ratio of a number of micromirrors in the first orientation in the masked portion of the dynamic amplitude mask to a number of micromirrors in the second orientation in the masked portion of the dynamic amplitude mask.

5. The ophthalmic imaging device according to claim 3, wherein each of the micromirrors is a digital micromirror device, DMD.

6. The ophthalmic imaging device according to claim 1, wherein the dynamic amplitude mask comprises an array of liquid crystal cells, wherein a liquid crystal in each liquid crystal cell of the array is individually switchable between a first phase, wherein the liquid crystal cell transmits light incident thereon towards to the light detector, and a second phase, in which the liquid crystal cell prevents light incident thereon from being transmitted to the light detector, wherein the unmasked portion of the dynamic amplitude mask consists of liquid crystal cells of the array having liquid crystals in the first phase, and the masked portion of the dynamic amplitude mask comprises at least some liquid crystal cells of the array having liquid crystals in the second phase.

7. The ophthalmic imaging device according to claim 6, wherein the masked portion of the dynamic amplitude mask comprises an interleaved arrangement of liquid crystal cells in the first phase and liquid crystal cells in the second phase, and the dynamic amplitude mask is configured to receive a ratio-setting signal and set, in accordance with the received ratio-setting signal, a ratio of a number of liquid crystal cells in the first phase in the masked portion of the dynamic amplitude mask to a number of liquid crystal cells in the second phase in the masked portion of the dynamic amplitude mask.

8. The ophthalmic imaging device according to claim 1, wherein the dynamic amplitude mask is located in at least one of an image plane of the ophthalmic imaging device, a Fourier plane of the ophthalmic imaging device or a plane in the ophthalmic imaging device which is between the image plane and the Fourier plane of the ophthalmic imaging device.

9. The ophthalmic imaging device according to claim 1, wherein the dynamic amplitude mask is arranged in the ophthalmic imaging device so as to receive light that is to form light beam scanned across the light guiding component by the scanning element, the unmasked portion of the dynamic amplitude mask is configured to allow a first portion of the received light, which is to form the light beam scanned across the light guiding component by the scanning element, to propagate to the scanning element, and the masked portion of the dynamic amplitude mask is configured to prevent at least some of the received light, which is to form the light beam scanned across the light guiding component by the scanning element, from propagating to the scanning element, and the ophthalmic imaging device further comprises a light intensity controller configured to control, as a function of the scan angle, an intensity of the light received by the dynamic amplitude mask, which is to form the light beam scanned across the light guiding component by the scanning element, such that the intensity of the light beam scanned across the light guiding component by the scanning element is substantially independent of the scan angle.

10. The ophthalmic imaging device according to claim 9, wherein the light intensity controller comprises:

a variable optical attenuator configured to attenuate light that is to be received by the dynamic amplitude mask and form the light beam scanned across the light guiding component by the scanning element, wherein the light intensity controller is configured to control the variable optical attenuator to vary the attenuation of the light as a function of the scan angle such that the intensity of the light beam scanned across the light guiding component by the scanning element is substantially independent of the scan angle.

11. The ophthalmic imaging device according to claim 1, wherein:

the masked portion and the unmasked portion of the dynamic amplitude mask are provided in a first region of a plane;

the dynamic amplitude mask further comprises a second unmasked portion configured to allow light from the first portion of the light beam, which has been reflected by the region of the eye and has passed through the unmasked portion of the dynamic amplitude mask, to propagate to the light detector, and a second masked portion having a spatial distribution which is configured to vary as a function as the scan angle such that the second masked portion prevents at least some of the light from the second portion of the light beam reflected back by the light guiding component and which has passed through the unmasked portion of the dynamic amplitude mask from reaching the light detector as the first portion of the light beam is scanned across the region of the eye, wherein the second masked portion and the second unmasked portion are provided in a second region of the plane that is separate from the first region; and the first region of the plane coincides with an image plane of the ophthalmic imaging device, and the second region of the plane coincides with a Fourier plane of the ophthalmic imaging device.

12. An ophthalmic imaging device for imaging an eye, comprising:

a scanning element arranged to scan at least a region of the eye with a light beam;

a light guiding component through which at least a first portion of the light beam is guided to scan across the region of the eye and then reflected back by the region by way of the light guiding component, wherein a second portion of the light beam is reflected back by the light guiding component without having scanned the eye;

a photodetector which is arranged in the ophthalmic imaging device to detect a spatial light intensity distribution, across a light-detection surface of the photodetector, of light incident on the light-detection surface, wherein the light comprises the first portion of the light beam which has been reflected back by the region by way of the light guiding component, and second portion of the light beam which has been reflected back by the light guiding component and which is incident on the photodetector with a spatial intensity distribution that varies as a function of a scan angle of the light beam scanned by the scanning element; and an image processor configured to process the spatial light intensity distribution detected by the photodetector by applying a digital mask to the spatial light intensity distribution to reduce values of detected light intensity in a masked portion of the detected spatial light intensity distribution that has been masked by the digital mask, and to generate image data based on the processed spatial light intensity distribution, wherein the masked portion has a spatial distribution which is configured to vary as a function of the scan angle so as to reduce a contribution of the second portion of the light beam reflected back by the light guiding component to the generated image data as the first portion of the light beam is scanned across the region of the eye.

13. The ophthalmic imaging device according to claim 12, wherein the image processor is configured to process the spatial light intensity distribution by applying the digital mask to the spatial light intensity distribution so as to set values of the detected light intensity in the masked portion of the detected spatial light intensity distribution to indicate zero light intensity, wherein the spatial distribution of the masked portion is configured to vary as the function of the scan angle so as to eliminate the contribution of light from the second portion of the light beam reflected back by the light guiding component to the generated image data as the first portion of the light beam is scanned across the region of the eye.

14. The ophthalmic imaging device according to claim 1, wherein a distribution of parts of the dynamic amplitude mask forming the masked portion is, for any scan angle, determined by the spatial intensity distribution, in a plane of the dynamic amplitude mask, of light reflected back by the light guiding component for that scan angle.

* * * * *